(12) United States Patent
Tang et al.

(10) Patent No.: US 11,584,713 B2
(45) Date of Patent: Feb. 21, 2023

(54) 25-HYDROXYCHOLECALCIFEROL MONOHYDRATE CRYSTAL, PREPARATION METHOD THEREFOR AND MICROEMULSION USING SAME

(71) Applicants: SHANDONG HAINENG BIOENGINEERING CO., LTD., Rizhao (CN); SHANDONG HAINENG PHARMACEUTICAL CO., LTD., Rizhao (CN)

(72) Inventors: Fei Tang, Rizhao (CN); Jindang Cao, Rizhao (CN); Xin Li, Rizhao (CN); Chao Zhang, Rizhao (CN); Hao Luo, Rizhao (CN); Qiangqiang Li, Rizhao (CN); Zhi Cao, Rizhao (CN); Liang Shu, Rizhao (CN)

(73) Assignees: SHANDONG HAINENG BIOENGINEERING CO., LTD., Rizhao (CN); SHANDONG HAINENG PHARMACEUTICAL CO., LTD., Rizhao (CN)

(*) Notice: Subject to any disclaimer, the term of this patent is extended or adjusted under 35 U.S.C. 154(b) by 58 days.

(21) Appl. No.: 16/986,592

(22) Filed: Aug. 6, 2020

(65) Prior Publication Data
US 2020/0361865 A1  Nov. 19, 2020

Related U.S. Application Data

(63) Continuation of application No. PCT/CN2018/099257, filed on Aug. 7, 2018.

(30) Foreign Application Priority Data

Feb. 6, 2018 (CN) .......................... 201810120581.0

(51) Int. Cl.
*C07C 401/00* (2006.01)
*A23K 20/174* (2016.01)
*A61K 9/107* (2006.01)

(52) U.S. Cl.
CPC .......... *C07C 401/00* (2013.01); *A23K 20/174* (2016.05); *A61K 9/1075* (2013.01); *C07B 2200/13* (2013.01)

(58) Field of Classification Search
CPC .............. A23V 2002/00; A23K 20/174; A61K 9/1075; C07C 401/00
USPC ......................................................... 514/167
See application file for complete search history.

(56) References Cited

U.S. PATENT DOCUMENTS

2006/0052350 A1* 3/2006 Ploutno ................... A61P 19/08
552/653
2011/0105444 A1 5/2011 Deluca et al.

FOREIGN PATENT DOCUMENTS

| CN | 107296152 A | 10/2017 |
| JP | 2005519894 A | 7/2005 |
| JP | 2008-504369 A | 2/2008 |
| JP | 2011529081 A | 12/2011 |
| WO | 2010/011906 A1 | 1/2010 |

OTHER PUBLICATIONS

Ma, "Advanced structural analysis", 2006, pp. 432-435; 7 pages including Partial English-language translation.
Search Report dated Mar. 3, 2021 in corresponding European Application No. 18905419.0; 8 pages.
Japanese Office Action dated Aug. 17, 2021 in corresponding Japanese Application No. 2020-564987; (14 pp., including machine-generated English translation).
Ashizawa; "A Polymorphism of Medicines and Crystallisation"; 2003, Issue 30 No. 3, Japanese Association for Crystal Growth; Maruzen Planetary Co., Ltd.; 34 pages (pp. 56-102 and 304-317) with English abstract.
International Search Report dated Oct. 17, 2018 in corresponding International application No. PCT/CN2018/099257; 4 pages.
Trinh-Toan et al., "Crystal Structure of 25-hydroxy -vitamin D3 Monohydrate: A Stereochemical Analysis of Vitamin D Molecule", Journal of the Chemical Society, 1988, pp. 393-401; 9pages.
Office Action dated Apr. 2, 2019 in corresponding Chinese application No. 201810120581.0; 8 pages.
Decision to Grant a Patent dated Apr. 12, 2022, in connection with corresponding Japanese Application No. 2020-564987 (5 pp., including machine-generated English translation).

* cited by examiner

*Primary Examiner* — Michael Barker
(74) *Attorney, Agent, or Firm* — Maier & Maier, PLLC

(57) ABSTRACT

A 25-hydroxycholecalciferol monohydrate crystal, a preparation method thereof, and a microemulsion using the 25-hydroxycholecalciferol monohydrate crystal. The X-ray powder diffraction spectrum of the 25-hydroxycholecalciferol monohydrate crystal of the present disclosure shows characteristic peaks at 2θ of 10.035°, 11.623°, 14.631°, 15.054°, 15.551°, 16.471°, 17.198°, 19.002°, 19.628°, 20.109°, 21.886°, 23.113°, 23.661°, 24.701°, 25.220°, 25.440°, and 28.527°. The 25-hydroxycholecalciferol monohydrate crystal can effectively enhance the stability of 25-hydroxycholecalciferol, and is more beneficial to the production and storage of related preparations, and thus biological characteristics of 25-hydroxycholecalciferol can be effectively utilized.

14 Claims, 5 Drawing Sheets

25-HYDROXYCHOLECALCIFEROL MONOHYDRATE CRYSTAL, PREPARATION METHOD THEREFOR AND MICROEMULSION USING SAME

CROSS-REFERENCE TO RELATED APPLICATIONS

This application is a continuation of International Application No. PCT/CN2018/099257, filed on Aug. 7, 2018, which claims priority of Chinese Patent Application No. 201810120581.0, filed on Feb. 6, 2018, both of which are hereby incorporated by reference in their entireties.

TECHNICAL FIELD

The present disclosure relates to a 25-hydroxycholecalciferol monohydrate crystal and, in particular, to a 25-hydroxycholecalciferol monohydrate crystal with a good stability and a preparation method thereof, and a microemulsion using the same.

BACKGROUND

Vitamin D3 itself has no physiological effect (H. F. De Luca et al., 1971). The $H^3$ labeled vitamin D3 is used to perform study, vitamin D3 that is absorbed in the intestine first undergoes hydroxylation of 25-carbon atom in the liver to produce 25-hydroxycholecalciferol, the 25-hydroxycholecalciferol is converted into 1,25-dihydroxy D3 in the kidney mitochondria and then delivered to the small intestine mucosa and the kidneys to promote absorption and reabsorption of two minerals, calcium and phosphorus, and meanwhile produce other functions required for animal body metabolism. Studies have shown that the 25-hydroxycholecalciferol has a different absorption principle from ester-soluble vitamins, and has a higher utilization efficiency.

25-hydroxycholecalciferol, also known as 25-hydroxyvitamin D3, is an expression type of activity of vitamin D3 in the body, with a structural formula as shown in formula 1.

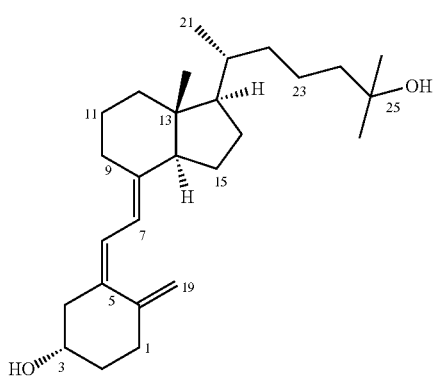

<Formula 1>

The 25-hydroxycholecalciferol may be obtained by any method. For example, U.S. Pat. No. 4,310,467 reported a method of isolation and purification of 25-hydroxycholecalciferol, CN10344301B reported for a method of preparation of 25-hydroxycholecalciferol by a photochemical reaction, CN103898004A reported a method of preparation of 25-hydroxycholecalciferol by fermentation, and U.S. Pat. No. 3,565,924 reported a method of production of 25-hydroxycholecalciferol. Furthermore, it was also reported in related research that 25-hydroxycholecalciferol may be utilized as an active ingredient in a feed. However, a stability test of 25-hydroxycholecalciferol showed that 25-hydroxycholecalciferol has a low stability, and after storage at 25° C. for one month, a content of 25-hydroxycholecalciferol is reduced from 99.23% to 65.03%. Therefore, how to enhance the stability of 25-hydroxycholecalciferol, so as to facilitate production, storage and use of relevant preparations, and thus make use of biological efficacy thereof, is an urgent problem in this field.

However, there is neither a report on 25-hydroxycholecalciferol monohydrate, nor a relevant literature recording the preparation of 25-hydroxycholecalciferol monohydrate from free 25-hydroxycholecalciferol as a raw material.

SUMMARY

In view of the abovementioned problem, the present disclosure provides a 25-hydroxycholecalciferol monohydrate crystal, a preparation method thereof, and a microemulsion using the same, which can effectively enhance the stability of 25-hydroxycholecalciferol, and is more beneficial to production and storage of related preparations, and thus biological properties of 25-hydroxycholecalciferol can be effectively utilized.

The present disclosure provides a 25-hydroxycholecalciferol monohydrate crystal, an X-ray powder diffraction spectrum of 25-hydroxycholecalciferol monohydrate crystal includes the following peaks:

| Peak | 2θ | d(A) | Peak area | Relative peak intensity (area %) |
|---|---|---|---|---|
| 1 | 10.035 | 8.8072 | 17530 | 18.0 |
| 2 | 11.623 | 7.6070 | 5192 | 5.3 |
| 3 | 14.631 | 6.0494 | 26181 | 26.8 |
| 4 | 15.054 | 5.8801 | 17698 | 18.1 |
| 5 | 15.551 | 5.6936 | 32676 | 33.5 |
| 6 | 16.471 | 5.3774 | 4111 | 4.2 |
| 7 | 17.198 | 5.1518 | 46646 | 47.8 |
| 8 | 19.002 | 4.6664 | 97630 | 100 |
| 9 | 19.628 | 4.5192 | 13767 | 14.1 |
| 10 | 20.109 | 4.4120 | 36305 | 37.2 |
| 11 | 21.886 | 4.0576 | 33575 | 34.4 |
| 12 | 23.113 | 3.8451 | 15163 | 15.5 |
| 13 | 23.661 | 3.7572 | 12429 | 12.7 |
| 14 | 24.701 | 3.6012 | 6838 | 7.0 |
| 15 | 25.220 | 3.5284 | 48909 | 50.1 |
| 16 | 25.440 | 3.4983 | 27121 | 27.8 |
| 17 | 28.527 | 3.1264 | 25633 | 26.3 |

It should be understood that, in general, when measuring a crystal by X-ray powder diffraction, there may be some small errors in peaks in the spectrogram due to differences in measuring instruments, measuring conditions and the like, and thus, other peak may also be included in the spectrogram of a crystal of the present disclosure in addition to the abovementioned peaks. The measuring conditions of the disclosure are as follows: Cu Kα line, tube voltage 40 kV, tube current 40 mA. FIG. 1 is an XRPD spectrogram of a 25-hydroxycholecalciferol monohydrate prepared in an embodiment of the present disclosure. The X-ray diffractometer (Bruker D8 advance) of FIG. 1 has working parameters as follows:

Cu Kα line; tube voltage: 40 kV; tube current: 40 mA; scanning type: fixed coupling; increase amount: 0.02°; scanning range: 3°-40°; scanning speed: 1 s/step.

A stability test shows that after the 25-hydroxycholecalciferol monohydrate crystal of the present disclosure is left open for six months at 25° C., a mass content of 25-hydroxycholecalciferol in the 25-hydroxycholecalciferol monohydrate crystal is 96.59%. Therefore, the 25-hydroxycholecalciferol monohydrate crystal of the present disclosure has a stable crystal property, which can effectively improve stability of 25-hydroxycholecalciferol.

Further, the 25-hydroxycholecalciferol monohydrate crystal provided in the present disclosure is obtained via a reaction between a 25-hydroxycholecalciferol solution and water; where the 25-hydroxycholecalciferol solution is obtained by dissolving 25-hydroxycholecalciferol in an organic solvent.

The 25-hydroxycholecalciferol monohydrate crystal is a product obtained via a hydration reaction of the 25-hydroxycholecalciferol solution. Where the 25-hydroxycholecalciferol solution is obtained by dissolving 25-hydroxycholecalciferol in an organic solvent. The present disclosure has no limitation on a source of 25-hydroxycholecalciferol raw material, which may be commercially available or prepared in-house.

The abovementioned organic solvent for preparation of the 25-hydroxycholecalciferol solution may be selected from one or more of an ether solvent, an alcohol solvent, a ketone solvent, and a chlorohydrocarbon solvent. Where the ether solvent includes, but is not limited to, tetrahydrofuran and 2-methyltetrahydrofuran; the alcohol solvent includes, but is not limited to, methanol, alcohol and isopropanol; the ketone solvent includes, but is not limited to, acetone and butanone; the chlorinated hydrocarbon solvent includes, but is not limited to, dichloromethane, chloroform and the like. When the organic solvent is a mixture of the above solvents, the present disclosure has no limitation on a ratio between various solvents. At the same time, when preparing the 25-hydroxycholecalciferol solution, a mass volume ratio of 25-hydroxycholecalciferol to the organic solvent is 1 g: 100 ml, and preferably 1 g: 5-40 ml, and more preferably 1 g: 5-20 ml.

When preparing the 25-hydroxycholecalciferol monohydrate crystal via a reaction of the 25-hydroxycholecalciferol solution with water, the present disclosure does not limit a reaction molar ratio of 25-hydroxycholecalciferol to water, and the reaction molar ratio may be 1: (0.6-2000), and preferably 1: (0.8-1.5), and more preferably 1: (1-1.2). When a molar amount of 25-hydroxycholecalciferol is greater than a molar amount of water, the 25-hydroxycholecalciferol monohydrate crystal has a too low yield; when a molar amount of 25-hydroxycholecalciferol is less than a molar amount of water, the 25-hydroxycholecalciferol monohydrate crystal will have a significantly increased yield. It is worth noting that, since 25-hydroxycholecalciferol has only one site for binding to water, even a molar amount of 25-hydroxycholecalciferol is less than a molar amount of water, the product is still a 25-hydroxycholecalciferol monohydrate crystal, and it is impossible to obtain a 25-hydroxycholecalciferol polyhydrate.

The present disclosure also provides a preparation method of the 25-hydroxycholecalciferol monohydrate crystal any one of embodiments above, including the following steps:

(1) heating and refluxing 25-hydroxycholecalciferol in an organic solvent until 25-hydroxycholecalciferol is dissolved to obtain a 25-hydroxycholecalciferol solution; and (2) adding water to the 25-hydroxycholecalciferol solution until a solid is precipitated to obtain the 25-hydroxycholecalciferol monohydrate crystal.

Specifically, after adding 25-hydroxycholecalciferol into the organic solvent, this reaction system is heated, so that the organic solvent is reflexed to dissolve 25-hydroxycholecalciferol. The organic solvent may be selected from one or more of the ether solvent, the alcohol solvent, the ketone solvent and the chlorohydrocarbon solvent mentioned above. After 25-hydroxycholecalciferol is dissolved, stirring is continued while heating is stopped, and water is slowly added to the 25-hydroxycholecalciferol solution until a white solid is precipitated out, and after addition of water is completed and a temperature of the system is reduced to room temperature, stirring is continued for 2-5 hours.

After the completion of stirring, a solid-liquid separation is performed on the system. Specifically, it is possible to collect a filter cake by means of centrifugation or filtration and dry the filter cake. In order to avoid detachment of crystal water in the 25-hydroxycholecalciferol monohydrate crystal, a drying temperature may be set less than 100° C., and preferably is set to 20-90° C., and more preferably 30-80° C.; the drying method may be an atmospheric pressure drying, and when there is a low drying temperature, drying under a reduced pressure may be selected in order to enhance drying effect. The present disclosure has no excessive requirement on the degree of drying, generally, moisture content is controlled to be less than 20 wt %, and preferably less than 10 wt %, and more preferably less than 5 wt %.

The preparation method for the 25-hydroxycholecalciferol monohydrate crystal of the present disclosure is simple and highly operable, and the 25-hydroxycholecalciferol monohydrate crystal obtained by the method has a high stability. A stability test shows that after the 25-hydroxycholecalciferol monohydrate crystal prepared by the method of the present disclosure is left open for six months at 25° C., a mass content of 25-hydroxycholecalciferol in the 25-hydroxycholecalciferol monohydrate crystal is 96.59%.

The present disclosure also provides a microemulsion, the microemulsion includes of the 25-hydroxycholecalciferol monohydrate crystal any one of embodiments above. Since 25-hydroxycholecalciferol is easily soluble in methanol, ethanol and dimethyl sulfoxide, slightly soluble in diethyl ether, and almost insoluble in water, a microemulsion containing 25-hydroxycholecalciferol has a very low solubility in water. Therefore, the solubility of microemulsion needs to be improved, so that it can be effectively absorbed in the body. Accordingly, the present disclosure provides a microemulsion containing a 25-hydroxycholecalciferol monohydrate crystal, the microemulsion having good stability and good water solubility.

Further, the microemulsion includes the following components by weight percentage: 0.05-1.25% of 25-hydroxycholecalciferol monohydrate crystal according to any one of embodiments above, 10-15% of Tween-60, 6-12% of sodium stearoyl lactate, 3-5% of Span-80, 1-2.5% of 2,6-di-tert-butyl-4-methylphenol, 0.2-1% of sorbic acid, 4-7% of propylene glycol and 56.25-75.75% of water.

Further, the microemulsion includes the following components by weight percentage: 0.125% of the 25-hydroxycholecalciferol monohydrate crystal according to any one of embodiments above, 12% of Tween-60, 8% of sodium stearoyl lactate, 4% of Span-80, 2.5% of 2,6-di-tert-butyl-4-methylphenol, 1% of sorbic acid, 7% of propylene glycol and 65.375% of water.

The microemulsion provided in the present disclosure may reach nanometer scale, and specifically, it may have an average particle size of up to 84-91 nm, and an encapsulation rate of up to 85-89%. The encapsulation rate refers to a percentage of an encapsulated substance (for example, a certain free drug) in a total amount of the drug in a liposome suspension. The encapsulation rate is an important indicator of mass control of liposomes and nanoparticles and reflects a degree to which a drug is encapsulated by a carrier. The encapsulation rate includes determinations of an encapsulation percentage and an encapsulation volume, and the encapsulation rate (EN %) is generally calculated by Equation 1 below:

$$EN\% = (1-Cf/Ct) \times 100\% \qquad \text{Equation 1}$$

in Equation 1, Cf is an amount of an encapsulated substance (a free drug); Ct is a total amount of drug in a nanoparticle or liposome suspension.

The present disclosure also provides a preparation method of the microemulsion according to any one of the embodiments above, including the following steps:

(1) mixing 0.05-1.25% of the 25-hydroxycholecalciferol monohydrate crystal according to any one of the embodiments above, 10-15% of Tween-60, 6-12% of sodium stearoyl lactate, 3-5% of Span-80, and 1-2.5% of 2,6-di-tert-butyl-4-methylphenol by weight percentage, and then heating to 45-55° C. for full dissolution, and oscillating well by using a vortex oscillator, to produce a first reaction solution;

(2) dissolving 4-7% of propylene glycol and 0.2-1% of sorbic acid into 56.25-75.75% of water by weight percentage at room temperature, and stirring well, to produce a second reaction solution; and (3) mixing the first reaction solution and the second reaction solution, and oscillating well by using the vortex oscillator, to prepare the microemulsion.

Generally, oscillating by the vortex oscillator for 10-15 min is sufficient to ensure homogeneous mixing of various components.

The present disclosure also provides a use of the microemulsion according to any one of the embodiments above in a feed additive, the microemulsion as the feed additive can shorten metabolic time of vitamin D3 in bodies of livestock and poultry, promote absorption and reabsorption of calcium and phosphorus elements, and fill a blank of using 25-hydroxycholecalciferol as the feed additive in domestic.

The present disclosure also provides a feed, including the microemulsion according to any one of the embodiments above, the feed can effectively promote the absorption of calcium and phosphorus elements in bodies of livestock and poultry, and lay a foundation for healthy growth of livestock and poultry.

Embodiments of the present disclosure have at least the following advantages:

1. the 25-hydroxycholecalciferol monohydrate crystal of the present disclosure is a new crystal form of 25-hydroxycholecalciferol monohydrate;

2. the 25-hydroxycholecalciferol monohydrate crystal of the present disclosure has good stability, improving a stability of 25-hydroxycholecalciferol to some extent, which is beneficial for production, storage and use of related preparations and has a wide application prospect;

3. the preparation method of the 25-hydroxycholecalciferol monohydrate crystal of the present disclosure is simple and easy to control, and has mild reaction conditions, a stable process, a good reproducibility and a stable product quality, and is suitable for industrial large-scale production of the 25-hydroxycholecalciferol monohydrate crystal;

4. the microemulsion of the present disclosure contains the 25-hydroxycholecalciferol monohydrate crystal having good stability, good water solubility and wide application range; and 5. the present disclosure innovatively applies the microemulsion containing the 25-hydroxycholecalciferol monohydrate crystal to the field of feed production, which facilitates absorption of calcium and phosphorus elements in bodies of livestock and poultry and lays a foundation for the healthy growth of livestock and poultry.

BRIEF DESCRIPTION OF DRAWING(S)

DETAILED DESCRIPTION OF EMBODIMENTS

In order to make the purposes, technical solutions and advantages of the present disclosure more clear, technical solutions of the embodiments of the present disclosure will be described clearly and completely below in combination with the accompanying drawings of the embodiments of the present disclosure. Obviously, the described embodiments are merely part, but not all, of the embodiments of the present disclosure. Based on the embodiments of the present disclosure, all other embodiments acquired by those skilled in the art without any creative effort shall belong to the protection scope of the present disclosure.

Embodiment 1

Preparation of 25-hydroxycholecalciferol monohydrate crystal

A specific preparation method includes the following steps:

adding 1 kg of 25-hydroxycholecalciferol into 200 mL of acetone, stirring, heating and refluxing until the 25-hydroxycholecalciferol was fully dissolved; adding slowly 200 mL of water dropwise until a white solid was precipitated out, and then stopping heating and continuing stirring for 3 hours; filtering under an atmospheric pressure to collect a filter cake, and drying the filter cake under 60° C. for 10 h to obtain a 25-hydroxycholecalciferol monohydrate crystal. The inventor performed the following tests on the 25-hydroxycholecalciferol monohydrate crystal prepared in this embodiment.

1. The moisture content of the 25-hydroxycholecalciferol monohydrate crystal prepared in the present embodiment was 4.5%, which was obtained by Karl Fischer titration.

Figure 1:
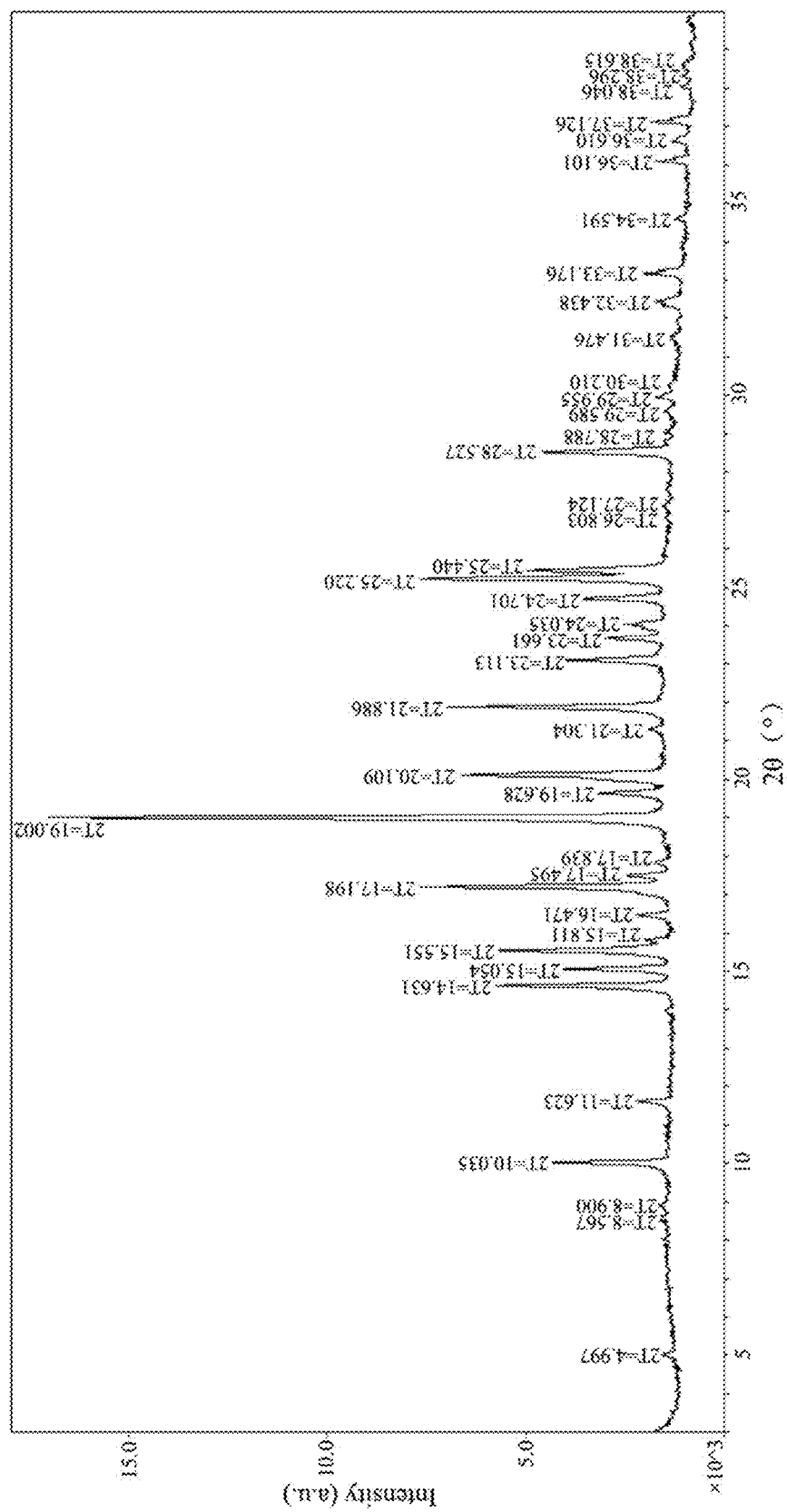
FIG. 1 is an XRPD spectrogram of a 25-hydroxycholecalciferol monohydrate crystal prepared in an embodiment of the present disclosure.

2. A typical X-ray powder diffraction (XRPD) was performed on the 25-hydroxycholecalciferol monohydrate crystal of the present embodiment via a Bruker D8 Advance X-ray diffractometer, where test conditions were that: Cu Kα line, tube Voltage 40 kV, and tube current 40 mA. FIG. 1 is an XRPD spectrogram of the 25-hydroxycholecalciferol monohydrate crystal prepared in the present embodiment of the present disclosure, and table 1 is relative data of the XRPD spectrogram of the 25-hydroxycholecalciferol monohydrate crystal prepared in the present embodiment of the present disclosure.

TABLE 1

Data of the XRPD spectrum of the 25-hydroxycholecalciferol monohydrate crystal

| Peak | 2θ | d(A) | Peak area | Relative peak intensity (area %) |
|---|---|---|---|---|
| 1 | 10.035 | 8.8072 | 17530 | 18.0 |
| 2 | 11.623 | 7.6070 | 5192 | 5.3 |
| 3 | 14.631 | 6.0494 | 26181 | 26.8 |
| 4 | 15.054 | 5.8801 | 17698 | 18.1 |
| 5 | 15.551 | 5.6936 | 32676 | 33.5 |
| 6 | 16.471 | 5.3774 | 4111 | 4.2 |
| 7 | 17.198 | 5.1518 | 46646 | 47.8 |
| 8 | 19.002 | 4.6664 | 97630 | 100 |
| 9 | 19.628 | 4.5192 | 13767 | 14.1 |
| 10 | 20.109 | 4.4120 | 36305 | 37.2 |
| 11 | 21.886 | 4.0576 | 33575 | 34.4 |
| 12 | 23.113 | 3.8451 | 15163 | 15.5 |
| 13 | 23.661 | 3.7572 | 12429 | 12.7 |
| 14 | 24.701 | 3.6012 | 6838 | 7.0 |
| 15 | 25.220 | 3.5284 | 48909 | 50.1 |
| 16 | 25.440 | 3.4983 | 27121 | 27.8 |
| 17 | 28.527 | 3.1264 | 25633 | 26.3 |

FIG. 1 and Table 1 verified that compositions of the 25-hydroxycholecalciferol monohydrate crystal prepared in the embodiment of the present disclosure, and a crystal form of 25-hydroxycholecalciferol is clearly characterized.

Figure 2:
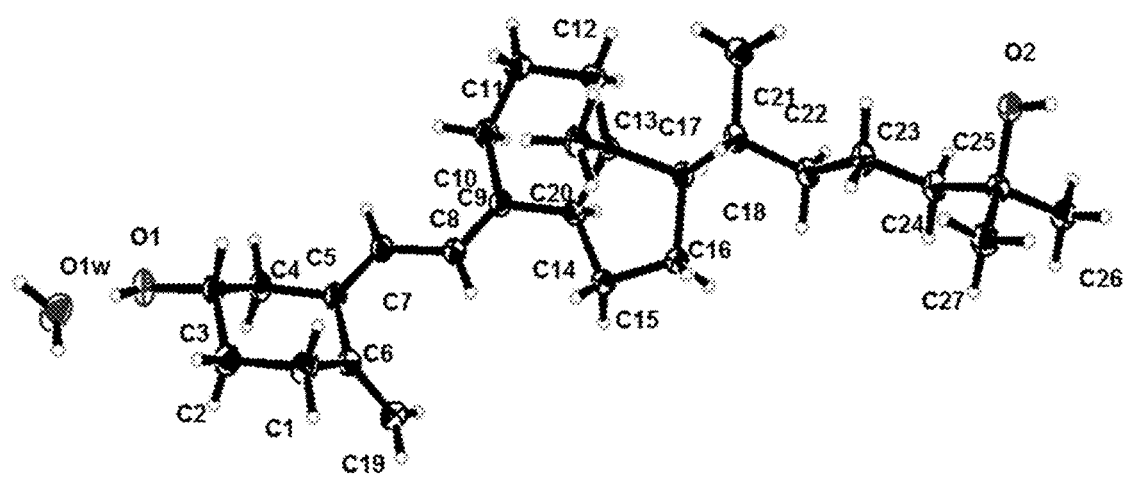
FIG. 2 is an atomic structural diagram of a 25-hydroxycholecalciferol monohydrate crystal prepared in an embodiment of the present disclosure.

3. Meanwhile, an atomic structure analysis was also performed on the 25-hydroxycholecalciferol monohydrate crystal prepared in the present embodiment of the present disclosure, and the results were shown in FIG. 2. FIG. 2 is an atomic structural diagram of the 25-hydroxycholecalciferol monohydrate crystal prepared in the present embodiment of the present disclosure. It can be seen from FIG. 2 that, in the 25-hydroxycholecalciferol monohydrate crystal prepared in the present embodiment of the present disclosure, a six-membered ring connected with 3-hydroxy is in a chair conformation and a bond connecting the 3-hydroxy with the six-membered ring is a flat bond.

4. An elemental analysis was performed on the 25-hydroxycholecalciferol monohydrate crystal prepared in the present embodiment of the present disclosure by using an elemental analyzer, where a content of C element was 77.22% and a content of hydrogen element was 11.10%. While according to the molecular formula of the 25-hydroxycholecalciferol monohydrate crystal, it was calculated that the content of C element was 77.46% and the content of hydrogen element was 11.08%.

Therefore, it can be known from the elemental analysis results that a product prepared by the present embodiment was the 25-hydroxycholecalciferol monohydrate crystal.

5. An nuclear magnetic resonance hydrogen spectroscopy, an nuclear magnetic resonance carbon spectroscopy and an electrospray mass spectrometry were performed on the 25-hydroxycholecalciferol monohydrate crystal prepared in the present embodiment, and the data are as follows:

$^1$H NMR (CDCl$_3$) δ: 6.22(d, J=11.3 Hz, 1H, 6-CH), 6.05(d, J=11.2 Hz, 1H, 7-CH), 5.08 (s, 1H, 19-CH), 4.81 (d, J=1.6 Hz, 1H, 19-CH), 3.96 (m, 1H, 3-CH), 2.80-2.85 (m, 1H), 2.55-2.58 (m, 1H), 2.39-2.43 (m, 1H), 2.29 (dd, J=7.6, 13.0 Hz, 1H), 2.15-2.23 (m, 1H), 1.22-2.02 (m, 22H),1.23 (s, 6H), 0.94 (d, J=6.4 Hz, 3H, 21-CH3), 0.55 (s, 3H, 18-CH$_3$).

$^{13}$C NMR (CDCl$_3$) δ: 144.95, 142.39, 134.99, 122.40, 117.40, 112.51, 71.18, 69.15, 56.33, 56.23, 45.81, 45.78, 44.30, 40.40, 36.28, 36.09, 35.05, 31.88, 29.31, 29.14, 28.95, 27.66, 23.52, 22.19, 20.71, 18.76, 11.96.

ESI-MS (m/z): 423.37[M+Na]$^+$, 823.78[2M+Na]$^+$.

6. Stability Test the 25-hydroxycholecalciferol monohydrate crystal prepared in the present embodiment was left open at 25° C., and a content of 25-hydroxycholecalciferol contained therein was tested after one month, three months and six months respectively, and meanwhile, 25-hydroxycholecalciferol was used as a control example, and the results were shown in Table 2.

The content of 25-hydroxycholecalciferol was measured by the following method: taking a sample to prepare a solution of about 10 μg/mL, injecting 20 μL for a HPLC analysis, and calculating the content thereof according to an external standard method.

Test conditions of the HPLC were as follows:

chromatographic column: C18 column; internal diameter: 4.6 mm; length: 150 mm, particle size: 5 μm;

detection wavelength: 265 nm;

temperature of column: 30° C.;

flow rate: 1.5 mL/min (which may be adjusted according to desired retention time and a degree of separation of 25-hydroxycholecalciferol and a 25-hydroxycholecalciferol precursor);

injection volume: 20 uL; and recording time: 2 times the retention time of main peak.

TABLE 2

Data of stability test of 25-hydroxycholecalciferol

| | Duration time of being left open | | | |
|---|---|---|---|---|
| | 0 day | One month | Three months | Six months |
| Content of 25-hydroxycholecalciferol of the present embodiment (%) | 99.60 | 99.05 | 98.46 | 96.59 |
| Content of 25-hydroxycholecalciferol of the control example (%) | 99.23 | 65.03 | 47.65 | 29.61 |

It can be known from table 2 that the 25-hydroxycholecalciferol monohydrate crystal prepared in the embodiment has a good stability, and there is almost no loss of 25-hydroxycholecalciferol therein after six months of being left open at 25° C.

Embodiment 2

Preparation of 25-hydroxycholecalciferol monohydrate microemulsion

A specific preparation method includes the following steps.

(1) Material Preparation 0.055 kg of the 25-hydroxycholecalciferol monohydrate crystal prepared in Embodiment 1, 10 kg of Tween-60, 10 kg of sodium stearoyl lactate, 5 kg of Span-80, 1 kg of BHT, 4 kg of propylene glycol, 0.2 kg of sorbic acid and 69.75 kg of water were taken.

(2) Preparation of a First Reaction Solution the 25-hydroxycholecalciferol monohydrate crystal was mixed with Tween-60, sodium stearoyl lactate, Span-80 and BHT, and heated to 50° C. for full dissolution, and then a vortex oscillating was performed by a vortex oscillator for 10 min to produce the first reaction solution.

(3) Preparation of a Second Reaction Solution at room temperature, propylene glycol and sorbic acid were dissolved in water and mixed well to produce the second reaction solution.

(4) Mixing the first reaction solution and the second reaction solution were mixed, and vortex oscillating was performed by a vortex oscillator for 10 min to produce a 25-Hydroxycholecalciferol monohydrate microemulsion. Where, the 25-hydroxycholecalciferol monohydrate in the microemulsion has a mass content of 0.055%.

It was detected that the 25-hydroxycholecalciferol monohydrate microemulsion prepared in the embodiment has a particle size of 84 nm, and an encapsulation rate of 89%.

Figure 3:
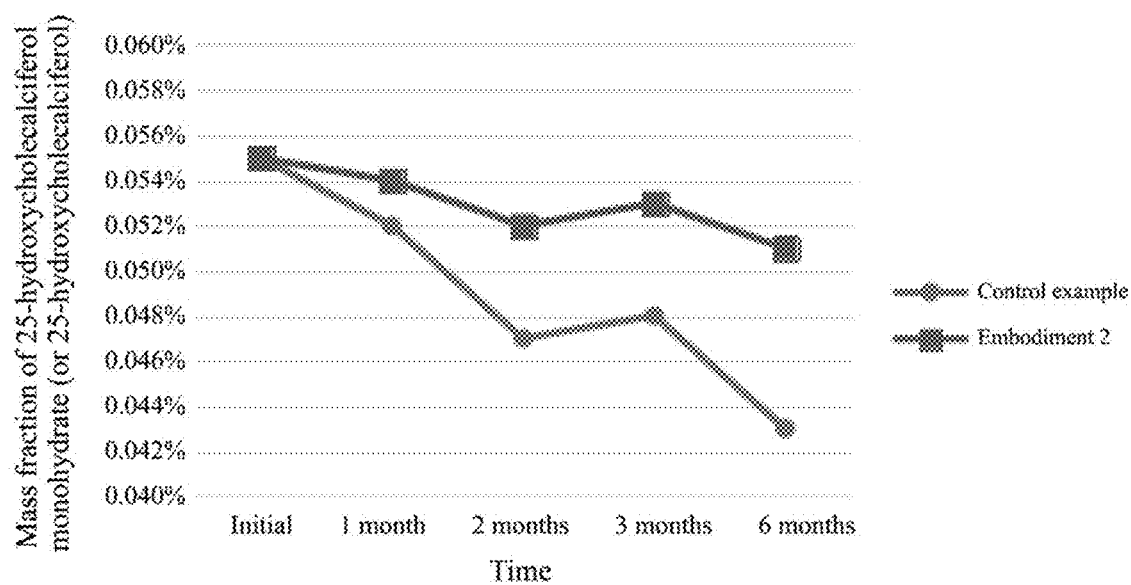
FIG. 3 is graphs of stability tests of a microemulsion prepared in embodiment 2 of the present disclosure and a microemulsion of a control example.

The microemulsion prepared in the embodiment was sealed and stored at 25° C., and the content of the 25-hydroxycholecalciferol contained therein was tested at one month, two months, three months and six months, and meanwhile, a microemulsion prepared from water-free 25-hydroxycholecalciferol by the same operation as the present embodiment was taken as a control example, and specific results were shown in FIG. 3. FIG. 3 is graphs of stability tests of the microemulsion prepared in Embodiment 2 of the present disclosure and the microemulsion of the control example. As shown in FIG. 3, a stability of the microemulsion prepared in the present embodiment is obviously better than that of the microemulsion prepared according to the prior art.

The content of 25-hydroxycholecalciferol was tested in the following method: when a date for stability test was due, taking a sample of about 10 μg/mL solution, injecting 20 μL for an HPLC analysis, and calculating the content thereof according to an external standard method.

Test conditions of the HPLC were as follows:

chromatographic column: C18 column; internal diameter: 4.6 mm; length: 150 mm, particle size: 5 μm;

detection wavelength: 265 nm;

temperature of column: 30° C.;

flow rate: 1.5 mL/min (which may be adjusted according to desired retention time and a degree of separation of 25-hydroxycholecalciferol and a 25-hydroxycholecalciferolprecursor);

injection volume: 20 uL; and recording time: 2 times the retention time of main peak.

Embodiment 3

Preparation of 25-hydroxycholecalciferol monohydrate microemulsion

A specific preparation method includes the following steps.

1) Material Preparation 0.135 kg (an effective mass of 0.125 kg) of 25-hydroxycholecalciferol monohydrate crystal prepared in Embodiment 1, 12 kg of Tween-60, 8 kg of sodium stearoyl lactate, 4 kg of Span-80, 2.5 kg of BHT, 7 kg of propylene glycol, 1 kg of sorbic acid and 65.375 kg of water were taken.

2) Preparation of a First Reaction Solution the 25-hydroxycholecalciferol monohydrate crystal was mixed with Tween-60, sodium stearoyl lactate, Span-80 and BHT, and heated to 45° C. for full dissolution, and then a vortex oscillating was performed by a vortex oscillator for 10 min to produce the first reaction solution.

3) Preparation of a Second Reaction Solution at room temperature, propylene glycol and sorbic acid were dissolved in water and mixed well to produce the second reaction solution.

4) Mixing the first reaction solution and the second reaction solution were mixed, and a vortex oscillating was performed by a vortex oscillator for 10 min to produce a 25-Hydroxycholecalciferol monohydrate microemulsion. Where the 25-hydroxycholecalciferol monohydrate in the microemulsion has a mass content of 0.125%.

It was detected that the 25-hydroxycholecalciferol monohydrate microemulsion prepared in the embodiment has a particle size of 86 nm, and an encapsulation rate of 88%.

Figure 4:
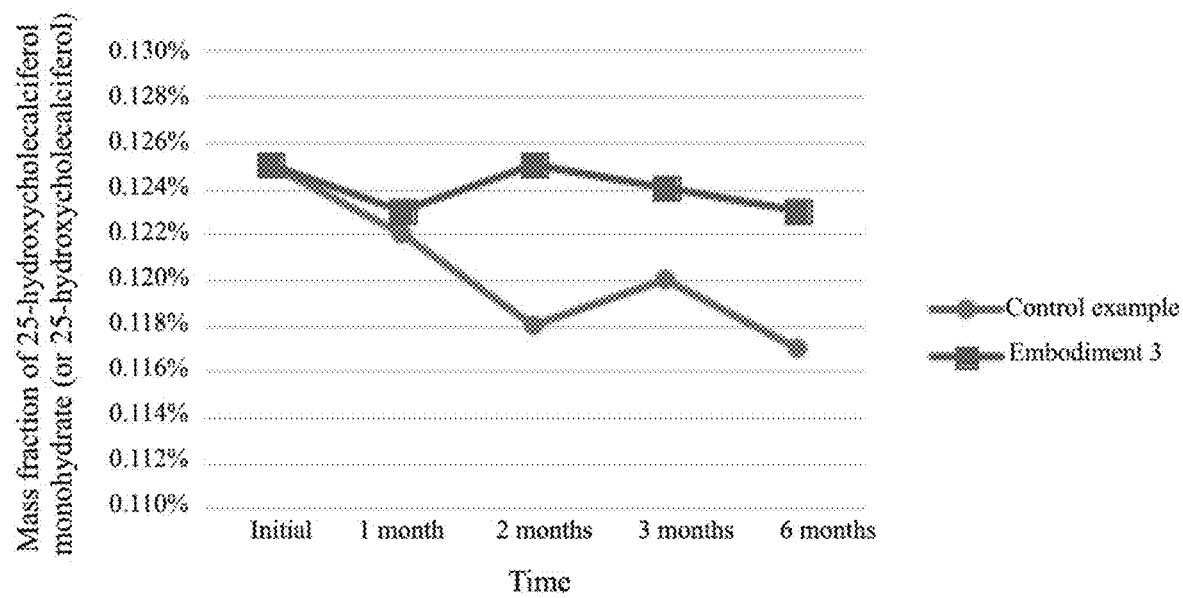
FIG. 4 is graphs of stability tests of a microemulsion prepared in embodiment 3 of the present disclosure and a microemulsion of a control example.

The microemulsion prepared in the embodiment was sealed and stored at 25° C., and the content of the 25-hydroxycholecalciferol contained therein was tested at one month, two months, three months and six months, and meanwhile, a microemulsion prepared from water-free 25-hydroxycholecalciferol by the same operation as the present embodiment was taken as a control example, and specific results were shown in FIG. 4. FIG. 4 is graphs of stability tests of the microemulsion prepared in Embodiment 3 of the present disclosure and the microemulsion of the control example. As shown in FIG. 4, a stability of the microemulsion prepared in the present embodiment is obviously better than that of the microemulsion prepared according to the prior art.

Embodiment 4

Preparation of 25-hydroxycholecalciferol monohydrate microemulsion

A specific preparation method includes the following steps.

(1) Material Preparation 1.30 kg (an effective mass of 1.25 kg) of the 25-hydroxycholecalciferol monohydrate crystal prepared in Embodiment 1, 15 kg of Tween-60, 12 kg of sodium stearoyl lactate, 5 kg of Span-80, 2.5 kg of BHT, 7 kg of propylene glycol, 1 kg of sorbic acid and 56.25 kg of water were taken.

(2) Preparation of a First Reaction Solution the 25-hydroxycholecalciferol monohydrate crystal was mixed with Tween-60, sodium stearoyl lactate, Span-80 and BHT, and heated to 55° C. for full dissolution, and then a vortex oscillating was performed by a vortex oscillator for 10 min to produce the first reaction solution.

(3) Preparation of a Second Reaction Solution at room temperature, propylene glycol and sorbic acid were dissolved in water and mixed well to produce the second reaction solution.

(4) Mixing the first reaction solution and the second reaction solution were mixed, and a vortex oscillating was performed by a vortex oscillator for 15 min to produce a 25-Hydroxycholecalciferol monohydrate microemulsion. Where the 25-hydroxycholecalciferol monohydrate in the microemulsion has a mass content of 1.25%.

It was detected that the 25-hydroxycholecalciferol monohydrate microemulsion prepared in the embodiment has a particle size of 91 nm, and an encapsulation rate of 85%.

Figure 5:
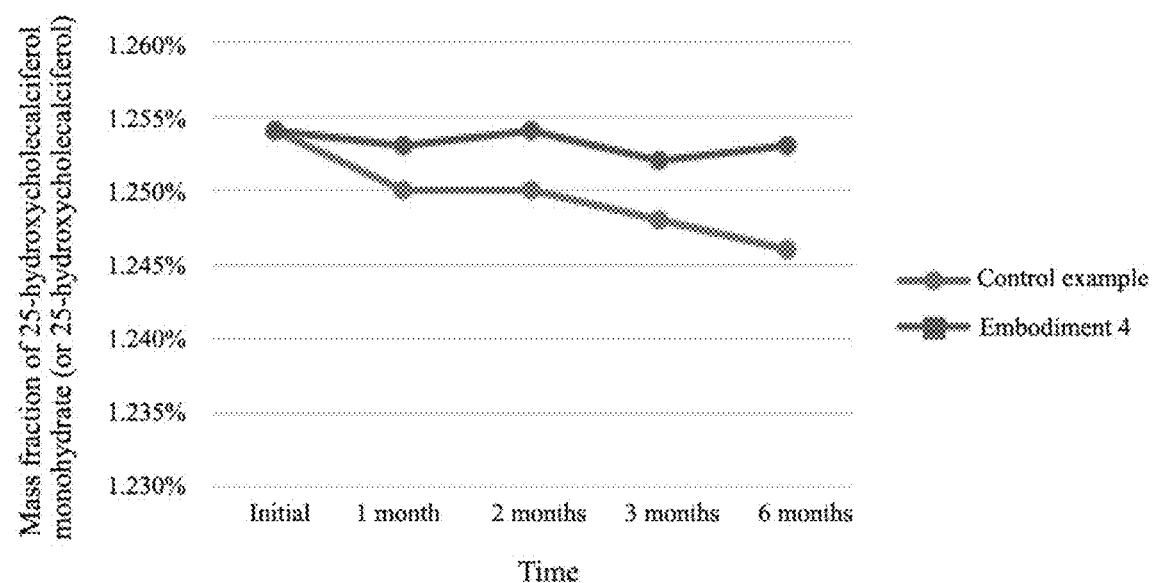
FIG. 5 is graphs of stability tests of a microemulsion prepared in embodiment 4 of the present disclosure and a microemulsion of a control example.

The microemulsion prepared in the embodiment was sealed and stored at 25° C., and the content of 25-hydroxycholecalciferol contained therein was tested at one month, two months, three months and six months, and meanwhile, a microemulsion prepared from water-free 25-hydroxycholecalciferol by the same operation as the present embodiment was taken as a control example, and specific results were shown in FIG. 5. FIG. 5 is graphs of stability tests of the microemulsion prepared in Embodiment 4 of the present disclosure and the microemulsion of the control example. As shown in FIG. 5, a stability of the microemulsion prepared in the present embodiment is obviously better than that of the microemulsion prepared according to the prior art.

Finally, it should be noted that: the above embodiments are only used for illustrating technical solutions of the present disclosure, but not being construed as limiting the present disclosure. Although the present disclosure is described in detail with reference to the forgoing embodiments, those ordinary skilled in the art should understand that modifications may still be made to the technical solutions of the forgoing embodiments or equivalent replacements may be made to part or all of the technical features therein. These modifications or replacements do not make the essence of corresponding technical solutions depart from the scope of the technical solutions of the embodiments of the present disclosure.

What is claimed is:

1. A 25-hydroxycholecalciferol monohydrate crystal, wherein an X-ray powder diffraction spectrum of 25-hydroxycholecalciferol monohydrate crystal comprises the following peaks:

| Peak | 2θ | d(Å) | Peak area | Relative peak intensity (area %) |
|---|---|---|---|---|
| 1 | 10.035 | 8.8072 | 17530 | 18.0 |
| 2 | 11.623 | 7.6070 | 5192 | 5.3 |
| 3 | 14.631 | 6.0494 | 26181 | 26.8 |
| 4 | 15.054 | 5.8801 | 17698 | 18.1 |
| 5 | 15.551 | 5.6936 | 32676 | 33.5 |
| 6 | 16.471 | 5.3774 | 4111 | 4.2 |
| 7 | 17.198 | 5.1518 | 46646 | 47.8 |
| 8 | 19.002 | 4.6664 | 97630 | 100 |
| 9 | 19.628 | 4.5192 | 13767 | 14.1 |
| 10 | 20.109 | 4.4120 | 36305 | 37.2 |
| 11 | 21.886 | 4.0576 | 33575 | 34.4 |
| 12 | 23.113 | 3.8451 | 15163 | 15.5 |
| 13 | 23.661 | 3.7572 | 12429 | 12.7 |
| 14 | 24.701 | 3.6012 | 6838 | 7.0 |
| 15 | 25.220 | 3.5284 | 48909 | 50.1 |
| 16 | 25.440 | 3.4983 | 27121 | 27.8 |
| 17 | 28.527 | 3.1264 | 25633 | 26.3 | the 25-hydroxycholecalciferol monohydrate crystal is obtained via a reaction of a 25-hydroxycholecalciferol solution with water; wherein the 25-hydroxycholecalciferol solution is obtained by dissolving 25-hydroxycholecalciferol in an organic solvent.

2. The 25-hydroxycholecalciferol monohydrate crystal according to claim 1, wherein the organic solvent is selected from one or more of an ether solvent, an alcohol solvent, a ketone solvent, and a chlorohydrocarbon solvent.

3. The 25-hydroxycholecalciferol monohydrate crystal according to claim 2, wherein a molar ratio of 25-hydroxycholecalciferol to water is 1:(0.6-2000).

4. The 25-hydroxycholecalciferol monohydrate crystal according to claim 3, wherein the molar ratio of 25-hydroxycholecalciferol to water is 1:(0.8-1.5).

5. A preparation method of the 25-hydroxycholecalciferol monohydrate crystal according to claim 1, comprising the following steps:

1) heating and refluxing 25-hydroxycholecalciferol in an organic solvent until 25-hydroxycholecalciferol is dissolved to obtain a 25-hydroxycholecalciferol solution; and 2) adding water to the 25-hydroxycholecalciferol solution until a solid is precipitated out to prepare the 25-hydroxycholecalciferol monohydrate crystal.

6. The preparation method of the 25-hydroxycholecalciferol monohydrate crystal according to claim 5, wherein the organic solvent is selected from one or more of an ether solvent, an alcohol solvent, a ketone solvent, and a chlorohydrocarbon solvent.

7. The preparation method of the 25-hydroxycholecalciferol monohydrate crystal according to claim 6, wherein step 2) further comprises:

adding water to the 25-hydroxycholecalciferol solution while stirring until a solid is precipitated out, continuing to stir, and after being cooled to room temperature, filtering to obtain a filter cake, and drying the filter cake until moisture content in the filter cake is less than 20 wt %, to prepare the 25-hydroxycholecalciferol monohydrate crystal.

8. A microemulsion, comprising the 25-hydroxycholecalciferol monohydrate crystal according to claim 1.

9. The microemulsion according to claim 8, comprising the following components by weight percentage: 0.05-1.25% of the 25-hydroxycholecalciferol monohydrate crystal 10-15% of Tween-60, 6-12% of sodium stearoyl lactate, 3-5% of Span-80, 1-2.5% of 2,6-di-tert-butyl-4-methylphenol, 0.2-1% of sorbic acid, 4-7% of propylene glycol and 56.25-75.75% of water.

10. The microemulsion according to claim 9, comprising the following components by weight percentage: 0.125% of the 25-hydroxycholecalciferol monohydrate crystal 12% of Tween-60, 8% of sodium stearoyl lactate, 4% of Span-80, 2.5% of 2,6-di-tert-butyl-4-methylphenol, 1% of sorbic acid, 7% of propylene glycol, and 65.375% of water.

11. The microemulsion according to claim 8, wherein the microemulsion is a nanometer microemulsion.

12. The microemulsion according to claim 11, wherein the microemulsion has an average particle size of 84-91 nm, and an encapsulation rate of 85-89%.

13. A preparation method of the microemulsion according to claim 8, comprising the following steps:

(1) mixing 0.05-1.25% of the 25-hydroxycholecalciferol monohydrate crystal 10-15% of Tween-60, 6-12% of sodium stearoyl lactate, 3-5% of Span-80, 1-2.5% of 2,6-di-tert-butyl-4-methylphenol by weight percentage, and then heating to 45-55° C. for full dissolution, and oscillating well by using a vortex oscillator, to produce a first reaction solution;

(2) dissolving 4-7% of propylene glycol and 0.2-1% of sorbic acid in 56.25-75.75% of water by weight percentage at 25±5° C., and stirring well, to produce a second reaction solution; and (3) mixing the first reaction solution and the second reaction solution, and oscillating well by using a vortex oscillator, to prepare the microemulsion.

14. A feed additive, comprising the microemulsion according to claim 8.

* * * * *